United States Patent [19]

Butler et al.

[11] Patent Number: 4,562,195

[45] Date of Patent: Dec. 31, 1985

[54] REVERSING AMNESIA WITH SATURATED TRICYCLIC NITROGEN-CONTAINING DIONES

[75] Inventors: Donald E. Butler, Ann Arbor; Yvon J. L'Italien, Plymouth, both of Mich.

[73] Assignee: Warner-Lambert Company, Morris Plains, N.J.

[21] Appl. No.: 687,182

[22] Filed: Jan. 7, 1985

Related U.S. Application Data

[63] Continuation-in-part of Ser. No. 576,232, Feb. 2, 1984, abandoned.

[51] Int. Cl.$^4$ .................... A61K 31/47; C07D 455/04
[52] U.S. Cl. ...................... 514/294; 546/93; 546/94; 548/428; 514/411
[58] Field of Search ............... 546/95, 93, 94; 424/258; 548/248, 428; 514/294, 411

[56] References Cited

U.S. PATENT DOCUMENTS 4,198,414  4/1980  Munson ..................... 546/94 X

FOREIGN PATENT DOCUMENTS 1242175  8/1971  United Kingdom .............. 546/94
2086905A  5/1982  United Kingdom .............. 546/95

OTHER PUBLICATIONS

Morrison & Boyd, *Organic Chemistry*, 3rd Ed. (1975), pp. 986–988; 746; 735.

*Primary Examiner*—Richard A. Schwartz
*Attorney, Agent, or Firm*—Jerry F. Janssen

[57] ABSTRACT

A class of novel saturated, fused-ring, tricyclic, nitrogen-containing diones are useful as agents in treating electro-convulsive shock-induced amnesia. A method of preparing the compounds, pharmaceutical compositions including the compounds, and a method of treating amnesia are disclosed.

22 Claims, No Drawings

REVERSING AMNESIA WITH SATURATED TRICYCLIC NITROGEN-CONTAINING DIONES

CROSS-REFERENCE TO RELATED APPLICATIONS

This application is a continuation-in-part of copending application Ser. No. 576,232 filed Feb. 2, 1984, now abandoned.

BACKGROUND OF THE INVENTION

The present invention relates to compounds and pharmaceutical compositions useful in the reversal of electroconvulsive shock-induced amnesia. More particularly, it is concerned with certain saturated tricyclic nitrogen-containing diones, with a method of preparing such compounds, pharmaceutical compositions including these compounds, and a method of reversing electroconvulsive shock-induced amnesia.

SUMMARY AND DETAILED DESCRIPTION

In one of its aspects, the present invention relates to compounds having the structural formula I:

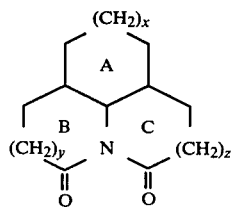

wherein x is zero, one, two, or three, and y and z are independently zero or one including the geometrical and stereochemical isomers thereof.

Compounds of the present invention, represented by structure I, comprise a class of structurally related saturated tricyclic nitrogen-containing fused-ring compounds. The present invention contemplates compounds where rings B and C (as indicated above) may independently be five- or six-membered rings. Ring A may be five-, six-, seven-, or eight-membered. Although structurally similar, the nomenclature of the class of compounds encompassed by the present invention is somewhat complex. The names of the compounds are based in part on the names of the corresponding unsaturated nitrogen-containing fused-ring systems.

The compounds of this invention exist in a variety of structural modifications. These include compounds where ring A is five-, six-, seven-, or eight-membered (i.e., where x is zero, one, two, or three, respectively) and rings B and C are independently five-membered (i.e., where y or z are zero).

In addition, the stereochemistry of the ring junctures between the fused rings may be either cis or trans. This latter possibility for geometrical isomerism is limited to some extent by the difficulty of forming trans-ring junctures in fused-ring systems involving five-membered lactam rings. For example, it is apparently not possible to synthesize structures on which a five-membered lactam ring is joined in a trans-configuration to another five-membered ring. The stereochemistry of the ring-junctures are indicated in the names of the compounds by the use of the Greek letters "alpha" or "beta" as illustrated by the following structural formula for one representative compound of the present invention:

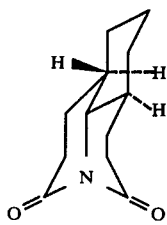

Octahydro-4H-pyrrolo[3,2,1-ij]quinoline-2,4-1H-dione (6a.alpha.,9a.alpha.,9b.beta.)

Further, for those compounds of the present invention in which the molecule has no plane of symmetry, stereoisomerism is possible.

The present invention contemplates all possible ring-size variants, geometric isomers, and stereo-isomers of the compounds depicted generically by structural formula I given above.

The terms "stereoisomers", "stereoisomerism", "optical isomerism", "optical isomers", "geometrical isomerism", and "geometrical isomers" as used throughout this specification and appended claims are those commonly employed by practitioners of the organic chemical art, specifically as defined on pages 1-6 of Eliel, "Stereochemistry of Carbon Compounds," McGraw-Hill, New York, 1962, incorporated herein by reference.

Examples of compounds falling within the scope of the present invention include, but are not necessarily limited to, the following compounds and their stereoisomers.

Hexahydro-2H-cyclopenta[gh]pyrrolizine-2,4(1H)-dione (5aα, 7aα, 7bα).
Octahydrocyclopent[hi]indolizine-2,4-dione (6aα, 8aα, 8bα).
Octahydrocyclopent[hi]indolizine-2,4-dione (6aα, 8aβ, 8bβ).
Hexahydro-1H-cyclopenta[ij]quinolizine-3,5-(2H,6H)-dione (7aα, 9aα, 9bα).
Hexahydro-1H-cyclopenta[ij]quinolizine-3,5(2H,6H)-dione (7aα, 7aα, 9bβ).
Hexahydro-1H-cyclopenta[ij]quinolizine-3,5(2H,6H)-dione (7aα, 9aβ, 9bα).
Hexahydropyrrolo[3,2,1-hi]indole-2,4(1H,5H)-dione (5aα, 8aα, 8bα).
Hexahydropyrrolo[3,2,1-hi]indole-2,4(1H,5H)-dione (5aα, 8aβ, 8bα).
Hexahydropyrrolo[3,2,1-hi]indole-2,4(1H,5H)-dione 5aα, 8aα, 8bβ).
Octahydro-4H-pyrrolo[3,2,1-ij]quinoline-2,4(1H)-dione (6aα, 9aα, 9bα).
Octahydro-4H-pyrrolo[3,2,1-ij]quinoline-2,4(1H)-dione (6aα, 9aα, 9bβ).
Octahydro-4H-pyrrolo[3,2,1-ij]quinoline-2,4(1H)-dione (6aα, 9aβ, 9bα).
Octahydro-4H-pyrrolo[3,2,1-ij]quinoline-2,4(1H)-dione (6aα, 9aβ, 9bβ).
Decahydro-3H,5H-benzo[ij]quinolizine-3,5-dione (7aα, 10aα, 10bα).
Decahydro-3H,5H-benzo[ij]quinolizine-3,5-dione (7aα, 10aβ, 10bα).
Decahydro-3H,5H-benzo[ij]quinolizine-3,5-dione 7aα, 10aα, 10bβ).
Octahydro-2H-cyclohepta[gh]pyrrolizine-2,4(1H)-dione (5aα, 9aα, 9bα).

Octahydro-2H-cyclohepta[gh]pyrrolizine-2,4(1H)-dione (5α, 9aβ, 9bα).

Octahydro-2H-cyclohepta[gh]pyrrolizine-2,4(1H)-dione (5α, 9aα, 9bβ).

Octahydrocycloocta[gh]pyrrolizine-2,4(1H, 5H)-dione (5α, 10aα, 10bα).

Octahydrocycloocta[gh]pyrrolizine-2,4(1H, 5H)-dione (5α, 10aβ, 10bα).

Octahydrocycloocta[gh]pyrrolizine-2,4-(1H, 5H)-dione (5aβ, 10aβ, 10bα).

The compounds of this invention where x, y, and z are zero or one, are prepared by the following general Synthesis Scheme 1. 2,6-Disubstituted cyclohexanone or 2,5-disubstituted cyclopentanone compounds of general formula III, where x, y, and z are independently zero or one, and R and R' are independently hydrogen, alkyl of from one to six carbon atoms (including t-butyl) or benzyl, are converted to the oxime, alkoxime, or N,N-dimethylhydrazone derivatives, VI, by reaction with hydroxylamine, or the corresponding O-alkyl-substituted alkoxylamine IV, or N,N-dimethylhydrazine, V, where R" is hydrogen or alkyl of from one to six carbon atoms.

The starting ketone diesters or diacids (III) are readily produced by the general method discovered by Openshaw and Robinson, *J. Chem. Soc.*, 941 (1937), and applied to cyclopentanone derivatives by Chaterjee, et al., *J. Ind. Chem. Soc.*, 17:161 (1940); *Science and Culture*, 6:724 (1941).

Compounds of type V, i.e. oxime diesters, have been prepared as intermediates by Leonard and Middleton, in their synthesis of the totally reduced (non-oxo-containing) tricyclic nitrogen compounds, *J. Amer. Chem. Soc.*, 74:5114 (1952).

Catalytic reduction of the oxime derivatives V by hydrogen over, for example, rhodium/carbon catalyst cyclizes the oxime derivatives to produce the bicyclic lactam esters VII, with some attendant production of the corresponding lactam acids (VIIa or VIIb where R or R' is hydrogen).

Synthetic Scheme 1

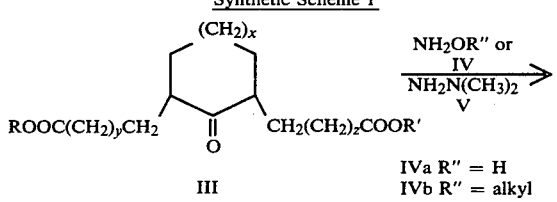

IVa R" = H
IVb R" = alkyl

III

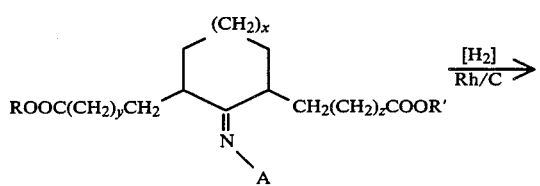

VIa A = —OH
VIb A = —O—alkyl
VIc A = —N(CH$_3$)$_2$

-continued
Synthetic Scheme 1

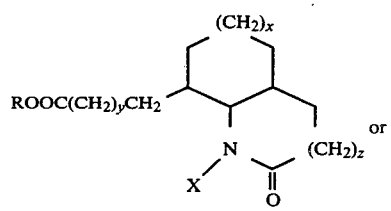

VIIa

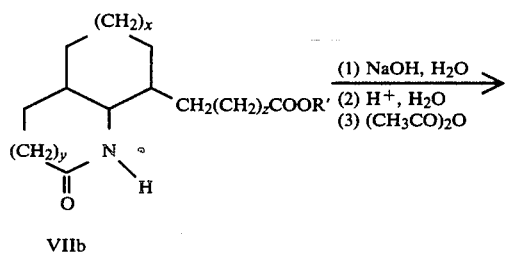

VIIb

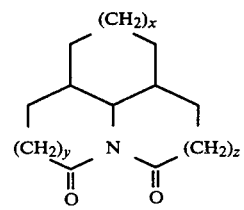

I

In those cases where y and z are different, the closure of the first lactam ring appears to favor six-membered ring formation over five-membered ring formation. However, the nature of the ester alkyl leaving group apparently also plays a role in the preference for which ring initially closes in this reaction.

Saponification of the lactam esters, VI in dilute aqueous sodium hydroxide, followed by acidification produces the lactam acids which cyclize to the tricyclic compounds I by internal dehydration in the presence of, for example, acetic anhydride at about 100° C.

Compounds of the present invention where x is two or three and y and z are both zero are prepared by methods detailed in the following Synthesis Scheme 2.

The known cycloalkanones, VIII (where x=two or three) are reacted with pyrrolidine in the presence of an acid, such as p-toluenesulfonic acid, to produce the enamine condensation products, IX. The enamines, IX, are reacted with methyl bromoacetate in a polar solvent such as acetonitrile, containing an acid-acceptor such as di-isopropyl-ethylamine to produce the intermediates, X, which are not isolated. The intermediates when x is two is converted by aqueous acid during work-up to the cycloheptanone-2,7-diacetic acid ester, XI.

Synthetic Scheme 2

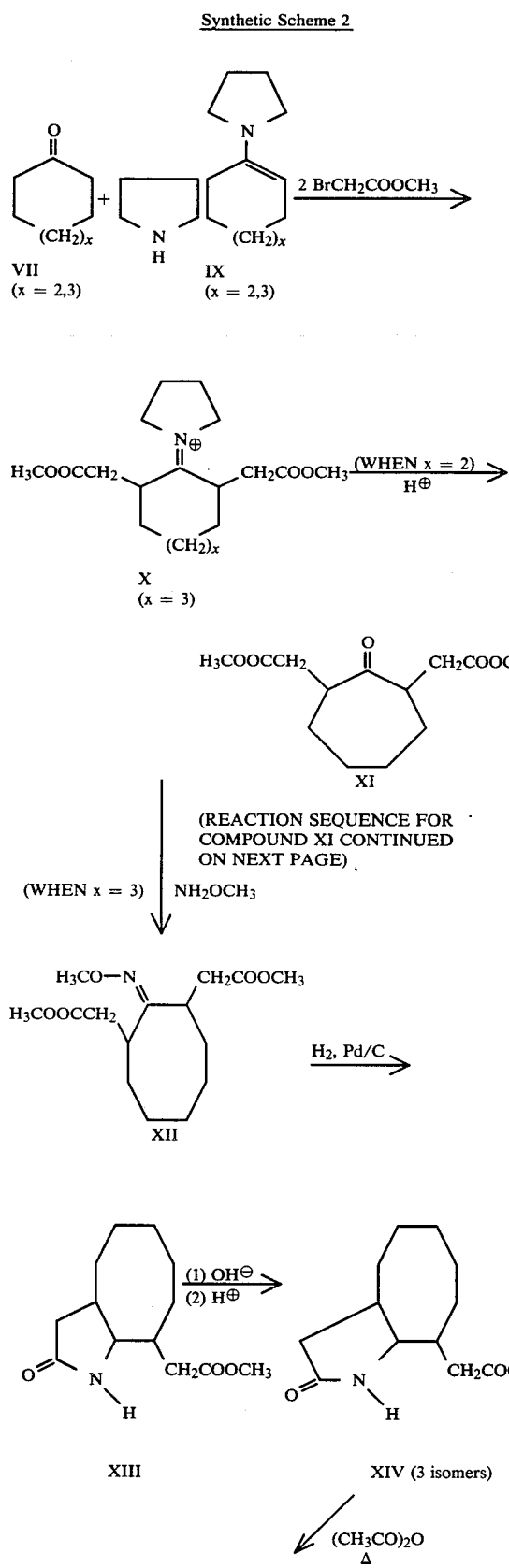

-continued
Synthetic Scheme 2

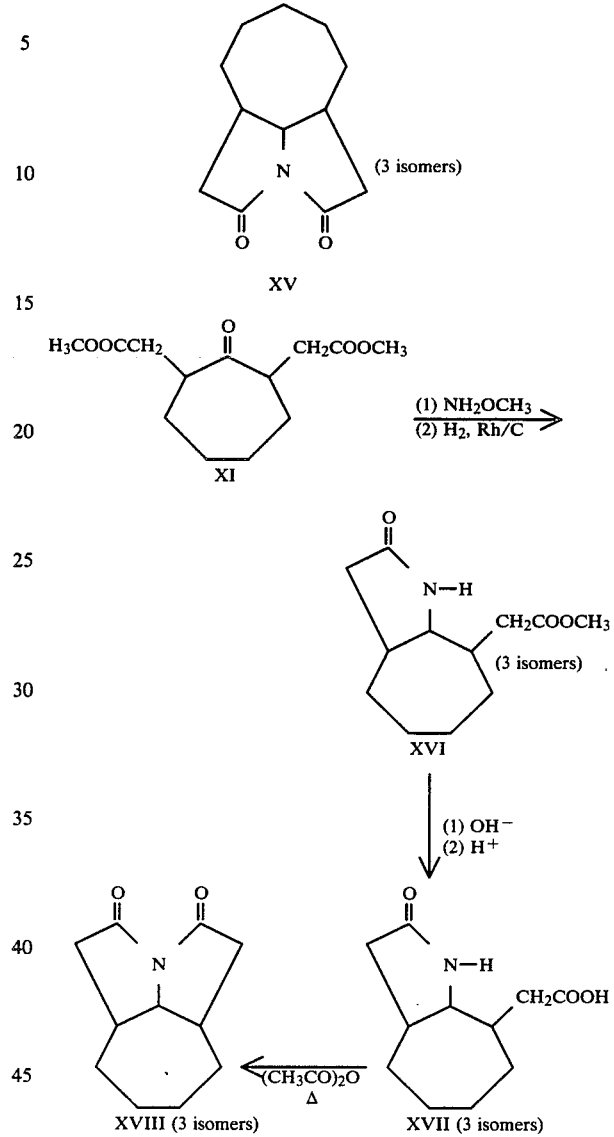

The di-ester, XI, is converted first, by reaction with methoxyamine to the corresponding O-methyl oxime (which is not isolated, and then subsequently by catalytic hydrogenation to the lactam ester, XVI. Upon ring closure to produce the lactam ring in XVI three isomers are generated, corresponding to the cis or trans relationship of the two carbon atoms and the nitrogen atom attached to the cycloheptane ring.

The lactam ester, XVI, is next saponified in the conventional manner with a dilute aqueous base, such as sodium hydroxide, and then acidified to produce the lactam acid, XVII. Heating XVII in a dehydrating agent such as, for example, acetic anhydride, produces compound XVIII which is, in fact, a compound in accordance with the present invention of formula I, above, where x=2, and y and z are both zero.

Alternatively, when X=3, intermediate X is converted to the O-methyloxime, XII, by reaction with methoxyamine. Subsequently, by catalytic reduction, the diester oxime, XII, is converted directly to the lactam acid methyl ester, XIII, and by conventional saponification followed by acidification to the lactam acid XIV. As with compound XV, there are three isomers of compound XIII corresponding to the cis or trans relationship of the two carbon atoms and the nitrogen atom attached to the cyclooctane ring.

Thermal cyclization in the conventional manner of XVIII by means of a dehydrating agent such as acetic anhydride produces XV which is a compound in accordance with structural formula I above where x=3 and y and z are both zero.

Also in accordance with the present invention, pharmaceutical compositions may be produced by formulating compounds having structural formula I above in unit dosage form with a pharmaceutically acceptable carrier. Some examples of unit dosage forms are tablets, capsules, lozenges, and pills; as well as powders and aqueous and nonaqueous solutions and suspensions packaged in containers containing either one, or some larger number of dosage units and capable of being subdivided into individual doses by such means as measurement into a teaspoon or other standard container.

Some examples of suitable pharmaceutical carriers, including pharmaceutical diluents, are sugars such as lactose and sucrose; starches such as corn starch and potato starch; cellulose derivatives such as sodium carboxymethylcellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; as well as other compatible substances normally employed in pharmaceutical formulations.

The pharmaceutical compositions of this invention can also contain other components such as coloring agents, flavoring agents, and/or preservatives. These latter materials, if present, are generally used in relatively small amounts. The compositions can, if desired, also contain other therapeutic agents, including other cognition activating agents such as 3-phenoxypyridine, and N-[N'N'-diisopropylaminoethyl]pyrrolidine-2-oxo-1-acetamide.

The percentage of active ingredient in the foregoing compositions can be varied within wide limits, but for practical purposes, the active ingredient is preferably present in a concentration of a least 10% in a solid composition, and at least 2% in a primarily liquid composition. The most satisfactory compositions are those in which a much higher proportion of the active ingredient is present. The pharmaceutical compositions of this invention preferably contain from 0.1 to 250.0 mg, preferably from 1 to 25 mg of the active ingredient per dosage unit so that the entire amount to be administered during a day can be made from a reasonable number of dose units.

The compounds of the present invention may exist as solids in anhydrous form as well as forms which are solvated with water, alcohols, and other pharmaceutically acceptable solvents. These solid forms may be incorporated into formulations intended for parenteral administration. Such formulations may be either in solution form or in powdered form intended for combination with an isotonic solution containing other ingredients such as preservatives, etc.

The solid forms of the compounds of this invention may also be incorporated into suppository formulations intended for rectal administration or into syrup formulations intended for oral administration.

The mammalian dose range for a 70 kg subject is from 1 to 1500 mg of compound per kg of body weight per day, preferably between about 25 mg to 750 mg per kg of body weight per day, optionally administered in portions.

The compounds of the present invention are useful for reversing the effects of electroconvulsive shock-induced amnesia. The effectiveness of these compounds was evaluated by a test designed to show the ability of a given substance to reverse amnesia induced by electroconvulsive shock. The test is more fully described in U.S. Pat. No. 4,154,347, issued March 20, 1979, and incorporated herein by reference. The only differences between the tests conducted in the present case and that described in the referenced patent were that in the present case, the test compounds were administered orally and the duration of the electrical shock used to induce amnesia in the test animals was 1.0 second.

The data from tests conducted employing compounds of the present invention appear in the following Table. The following criteria were used in interpreting the data: 40% or more amnesia reversal in the test animals=active, A; 25% to 39% amnesia reversal=borderline activity, C; 0% to 24% reversal of amnesia=inactive, N.

TABLE $$\begin{array}{c} (CH_2)_x \\ A \\ B \quad C \\ (CH_2)_y \quad N \quad (CH_2)_z \\ \parallel \quad \parallel \\ O \quad O \end{array}$$

Percent Amnesia Reversal of Orally Administered Test Compounds

| Compound | x | y | z | 100 | 10 | 1 | 0.1 |
|---|---|---|---|---|---|---|---|
| 1 | 0 | 0 | 0 | 50 (A) | 56 (A) | 62 (A) | — |
|   |   |   |   | 0 (N) | 0 (N) | 50 (A) | — |
| 2 | 1 | 0 | 0 | 46 (A) | 20 (N) | 54 (A) | — |
| 3* | 1 | 1 | 0 | 33 (C) | 42 (A) | 75 (A) | — |
| 4** | 1 | 1 | 0 | — | 61 (A) | 72 (A) | 91 (A) |
| 5 | 1 | 1 | 1 | 26 (C) | 75 (A) | 31 (C) | — |
| 6*** | 2 | 0 | 0 | 50 (A) | 43 (A) | 57 (A) | — |

*All ring junctures cis.
**A-B ring juncture trans, A-C ring juncture cis.
***Mixture of three isomers The following synthetic examples are provided to enable one skilled in the art to practice the present invention. These examples are not to be read as limiting the scope of the invention as it is defined by the appended claims, but merely illustrative thereof.

EXAMPLE 1

Preparation of cyclopentanone 2,5-diacetic acid dimethyl ester O-methyloxime

Cyclopentanone 2,5-diacetic acid (synthesized in J. Ind. Chem. Soc., 17, 161–166 (1947), (20 g (0.1 mol)), in 200 ml of methanol is saturated with gaseous hydrogen chloride. The solution is refluxed for 16 hours and is concentrated under reduced pressure. The residual oil is distilled to yield cyclopentanone 2,6-diacetic acid dimethyl ester with a boiling point of 110°–112° C. at 0.1 mm pressure. Cyclopentanone 2,6-diacetic acid dimethyl ester, 13.4 g (0.058 mol), is dissolved in 125 ml of pyridine and 5.3 g (0.065 mol) of methoxyamine hydrochloride is added portionwise with stirring under an atmosphere of nitrogen. The mixture is stirred 48 hours and diluted with 250 ml of water. The turbid mixture is extracted with five portions of 75 ml of chloroform. The combined extracts are dried over anhydrous magnesium sulfate. The dried extracts are filtered and concentrated to yield a residue of yield cyclopentanone 2,6-diacetic acid dimethyl ester O-methyloxime (VPC of this material=100% and it was used as such).

Preparation of octahydro-2-oxocyclopenta[b]pyrrole-6-acetic acid (3aα, 6β, 6aα),octahydro-2-oxocyclopenta[b]pyrrole-6-acetic acid (3aα, 6α, 6aα) and corresponding methyl esters A solution of 14.45 grams (0.055 mol) cyclopentanone 2,5-diacetic acid dimethyl ester O-methyl oxime is dissolved in 140 ml of methanol and is treated with hydrogen using a 10% rhodium on carbon (Rh/C) catalyst at 50 psi and 50° C. The mixture is filtered and concentrated at reduced pressure to yield a mixture of octahydro-2-oxocyclopenta[b]pyrrole-6-acetic acid methyl ester (3aα, 6β, 6aα) and octahydro-2-oxocyclopenta[b]pyrrole-2-oxo-6-acetic acid methyl ester (3aα, 6α, 6aα) and the corresponding acids. The acids can be separated from the esters by chromatography over SiO$_2$ using 5% 2-propanol in methylene chloride for elution. Fractional crystallization from anhydrous diethylether separates the isomeric esters. Octahydro-2-oxocyclopenta[b]pyrrole-6-acetic acid methyl ester (3aα, 6β, 6aα) has a melting point of 100°-110° C. and octahydro-2-oxocyclopenta[b]-pyrrole-6-acetic acid methyl ester (3aα, 6α, 6aα) has a melting point of 60°-100° C.

Hexahydro-2-oxocyclopenta[b]pyrrole-6-acetic acid methyl ester (3aα, 6β, 6aα), 2.2 g (0.011 m), is treated with 11 ml of 1N sodium hydroxide solution with stirring at 50° C. for 15 minutes. The reaction mixture is extracted with diethyl ether and the agueous layer is passed through a Dowex-acid column. Concentration of the eluate followed by filtration of the crystals yields hexahydro-2-oxocyclopenta[b]-pyrrole-6-acetic acid (3aα, 6β, 6aα) with a melting point of 186°-189° C.

Hexahydro-2-oxocyclopenta[b]pyrrole-6-acetic acid methyl ester (3aα, 6α, 6aα), 2.2 g (0.011 m) is treated with 11 ml of 1N sodium hydroxide solution with stirring at 50° C. for 15 minutes. The reaction mixture is extracted with diethyl ether and the aqueous layer is passed through a Dowex-acid column. Concentration of the eluate followed by filtration to collect the crystalline product yields hexahydro-2-oxocyclopenta[b]pyrrole-6-acetic acid (3aα, 6α, 6aα) with a melting point of 230°-232° C.

Preparation of hexahydro-2H-cyclopenta[gh]pyrrolizine-2,4(1H)-dione (5aα, 7aα, 7bα)

A solution of 1.7 g (0.0092 mol) of octahydro-2-oxocyclopenta[b]pyrrole-6-acetic acid (3aα, 6β, 6aα)] ("cis") and the corresponding "trans" isomer [octahydro-2-oxocyclopenta[b]pyrrole-6-acetic acid (3aα, 6α, 6aα) is prepared in 5.0 g of acetic anhydride. The mixture is stirred and refluxed ten minutes. The acetic acid and unreacted acetic anhydride is removed at reduced pressure and the residue is treated with anhydrous diethyl ether. The residue crystallizes. The desired hexahydro-2H-cyclopenta[gh]pyrrolizine-2,4(1H)-dione (5aα, 7aα, 7bα) is isolated with a melting point of 125°-127° C. after vacuum sublimation. Concentration of the solution yields octahydro-2-oxocyclopenta[b]pyrrole-6-acetic acid (3aα, 6α, 6aα) with a melting point of 230°-232° C.

EXAMPLE 2

Preparation of cyclohexanone 2,6-diacetic acid dimethyl ester O-methyloxime

A solution of 20.2 g (0.094 mol) cyclohexanone 2,6-diacetic acid (synthesized in *J. Ind. Chem. Soc.*, 24, 169-172 (1947)) in 200 ml of methanol is saturated with gaseous hydrogen chloride. The solution is refluxed for 16 hours and is concentrated under reduced pressure. The residual oil is distilled to yield cyclohexanone 2,6-diacetic acid dimethyl ester with a boiling point of 115°-120° C. at 0.1 mm pressure. Cyclohexanone 2,6-diacetic acid dimethyl ester, 15.8 g (0.065 mol), is dissolved in 125 ml of pyridine and 5.85 g (0.07 mol) of methoxyamine hydrochloride is added portionwise with stirring under an atmosphere of nitrogen. The mixture is stirred 48 hours and diluted with 250 ml of water. The turbid mixture is extracted with 5 portions of 75 ml of chloroform. The combined extracts are dried over anhydrous magnesium sulfate. The dried extracts are filtered, concentrated and the residue distilled to yield cyclohexanone 2,6-diacetic acid dimethyl ester O-methyloxime with a boiling point of 120°-125° C. at 0.3 mm pressure.

Preparation of octahydro-2-oxo-1H-indole-7-acetic acid methyl ester (3aα, 7β, 7aα) and octahydro-2-oxo-1H-indole-7-acetic acid methyl ester (3aα, 7α, 7aα)

A solution of 11.9 g (0.043 mol) cyclohexanone, 2,6-diacetic acid dimethyl ester O-methyl oxime is dissolved in 100 ml of methanol and is treated with hydrogen using a 10% rhodium on carbon (Rh/C) catalyst at 53.5 psi and 50° C. The mixture is filtered and concentrated at reduced pressure to yield a mixture of octahydro-2-oxo-1H-indole-7-acetic acid methyl esters (3aα, 7β, 7aα; and 3aα, 7α, 7aα). These can be separated by fractional crystallization using anhydrous diethyl ether into octahydro-2-oxo-1H-indole-7-acetic acid methyl ester (3aα, 7β, 7aα) with a melting point of 145°-148° C. and octahydro-2-oxo-1H-indole-7-acetic acid methyl ester (3aα, 7α, 7aα) with a melting point of 110°-120° C. The latter contained a small amount of the "all cis-isomer."

Preparation of octahydro-2-oxo-1H-indole-7-acetic acid (3aα, 7β, 7aα) and octahydro-2-oxo-1H-indole-7-acetic acid (3aα, 7α, 7aα)

A solution of 50 ml (0.05 mol) of 1N sodium hydroxide is added to a mixture of octahydro-2-oxo-1H-indole-7-acetic acid methyl esters (3aα, 7β, 7aα; and 3aα, 7α, 7aα) with stirring. The mixture is stirred and heated at 50° C. for 30 minutes. The mixture is cooled and extracted with diethyl ether and the basic aqueous phase is acidified with an equivalent of 2N hydrochloric acid. Alternatively the basic solution can be passed through a Dowex 50W-acid column and the acids isolated by freeze drying the filtrate. The mixture of octahydro-2-oxo-1H-indole-7-acetic acids (3aα, 7β, 7aα and 3aα, 7α, 7aα) has a melting point of 185°-215° C. and can be used as is in the cyclization procedure or separated by fractional crystallization from water. Octahydro-2-oxo-1H-indole-7-acetic acid (3aα, 7β, 7aα) has a melting of 230°–232° C. Octahydro-2-oxo-1H-indole-7-acetic acid (3aα, 7α, 7aα) has a melting point of 240°–242° C.

Preparation of hexahydropyrrolo[3,2,1-hi]indole-2,4(1H,5H)-dione (5aα, 8aα, 8bα)

A solution of 1.1 g (0.0055 mol) of a mixture of (3aα, 7α, 7aα) and (3aα, 7β, 7aα) forms of octahydro-2-oxo-1H-indole-7-acetic acid is prepared in 3.0 g of acetic anhydride. The mixture is stirred and refluxed ten minutes. The acetic acid and excess unreacted acetic anhydride is removed at reduced pressure. The residue is treated with anhydrous diethyl ether and the desired hexahydropyrrolo-[3,2,1-hi]indole-2,4(1H,5H)dione (5aα, 8aα, 8bα) is isolated as a crystalline solid with a melting point of 123°–125° C. after recrystallization from toluene. The unreacted (3aα, 7α, 7aα) form of octahydro-2-oxo-1H-indole-7-acetic acid is isolated by evaporation and trituration of the residue with ethyl acetate, with a melting point of 238°–240° C.

EXAMPLES 3 AND 4

Preparation of cyclohexanone 2-acetic acid 6-propanoic acid diethyl ester O-methyloxime Cyclohexanone 2-acetic acid 6-propanoic acid (synthesized in *J. Amer. Chem. Soc.*, 74, 5114 (1952)), 19.4 grams (0.085 mol), is dissolved in 200 ml of ethanol and is saturated with gaseous hydrogen chloride. The solution is refluxed for 16 hours and is concentrated under reduced pressure. The residual oil is distilled to yield cyclohexanone 2-acetic acid 6-propanoic acid diethyl ester. A solution of 56.8 g (0.2 mol) of cyclohexanone 2-acetic acid 6-propanoic acid diethyl ester in 500 ml of pyridine is treated with 21 g (0.25 mol) methoxyamine hydrochloride. The solution is stirred 36 hours and is poured into 1.5 l of water. The turbid mixture is extracted with five portions of 250 ml of chloroform. The combined extracts are dried over anhydrous magnesium sulfate. The extracts are filtered and concentrated to leave a residual oil of cyclohexanone 2-acetic acid 6-propanoic acid diethyl ester O-methyloxime which is used as such.

Preparation of (4aα, 8β, 8aα) and (4aα, 8α, 8aα) decahydro-2-oxo-8-quinolineacetic acids and ethyl esters A solution of 17.1 g (0.54 mol) cyclohexanone 2-acetic acid, 6-propanoic acid, diethyl ester O-methyl oxime is dissolved in 170 ml of methanol and is treated with hydrogen using a 10% rhodium on carbon (Rh/C) catalyst at 50 psi and 50° C. The solution is filtered and concentrated at reduced pressure to yield a mixture of (4aα, 8β, 8aα) and (4aα, 8α, 8aα) decahydro-2-oxo-8-quinolineacetic acid ethyl esters with a melting point of 195°–200° C. These are hydrolyzed by treatment with 1N sodium hydroxide followed by neutralization with 1N hydrochloric acid. Fractional crystallization from water allows separation of the cis-trans-mixture (mp=165°–180° C.) into (4aα, 8β, 8aα) decahydro-2-oxo-8-quinolineacetic acid ("cis") with a melting point of 210°–214° C. and (4aα, 8α, 8aα) decahydro-2-oxo-8-quinolineacetic acid ("trans") with a melting point of 235°–240° C.

Preparation of octahydro-4H-pyrrolo[3,2,1-ij]-quinoline-2,4(1H)-dione (6aα, 9aα, 9bα) and octahydro-4H-pyrrolo-[3,2,1-ij]-quinoline-2,4(1H)-dione (6aα, 9aβ, 9bβ)

A solution of 3.3 g (0.015 mol) of a mixture of (4aα, 8α, 8aα) and (4aα, 8β, 8aα) forms of decahydro-2-oxo-8-quinolineacetic acids is prepared in 15 g of acetic anhydride. The mixture is stirred and refluxed ten minutes. The unreacted acetic acid and acetic anhydride is removed at reduced pressure and the residue is treated with anhydrous diethyl ether. The residue crystallizes. The all cis product: octahydro-4H-pyrrolo[3,2,1-ij]quinoline-2,4(1H)-dione (6aα, 9aα, 9bα) with a melting point of 133°–135° C. is isolated by trituration of the residue with anhydrous diethyl ether. The residual product containing mostly octahydro-4H-pyrrolo[3,2,1-ij]-quinoline-2,4(1H)-dione (6aα, 9aβ, 9bβ) is purified by chromatography using silica gel on a Lobar column (elution with ethyl acetate) to yield pure octahydro-4H-pyrrolo[3,2,1-ij]quinoline-2,4(1H)dione (6aα, 9aβ, 9bβ) with a melting point of 118°–120° C.

EXAMPLE 5

Preparation of cyclohexanone 2,6-dipropanoic acid dimethyl ester O-methyloxime

A solution of 30 g (0.1 mol) of cyclohexanone 2,6-dipropanoic acid diethyl ester (synthesized in *J. Amer. Chem. Soc.*, 89, 217 (1963)) in 500 ml of pyridine is treated with 21 g (0.25 mol) methoxyamine hydrochloride. The solution is stirred 36 hours and poured into 1.5 l of water. The turbid mixture is extracted with five portions of 250 mg of chloroform. The combined extracts are dried over anhydrous magnesium sulfate. The extracts are filtered and concentrated to leave a residual oil of cyclohexanone 2,6-dipropanoic acid diethyl ester O-methyloxime which is used as such.

Preparation of (4aα, 8β, 8α) decahydro-2-oxo-8-quinolinepropanoic acid and ethyl ester ("cis")

A solution of 62.7 g (0.19 mol) of cyclohexanone 2,6-dipropanoic acid diethyl ester O-methyloxime in 630 ml of ethanol is treated with hydrogen using 10% rhodium on C at 50 psi and 50° C. The mixture is filtered and concentrated at reduced pressure to yield (4aα, 8β, 8aα) decahydro-2-oxo-8-quinolinepropanoic acid ethyl ester ("cis") with a melting point of 45°–50° C. after recrystallization from anhydrous diethyl ether and n-pentane (4aα, 8β, 8aα) decahydro-2-oxo-8-quinolinepropanoic acid ethyl ester ("cis"), 5.1 g (0.02 mol), is treated with 1N (0.02 mol) sodium hydroxide with stirring at 50° C. for 20 minutes. The solution is extracted with diethyl ether and the aqueous basic layer is acidified with 20 ml of (0.02 mol) of 1N hydrochloric acid. (4aα, 8β, 8aα) decahydro-2-oxo-8 quinolinepropanoic acid ("cis") crystallizes and after recrystallization from ethanol has a melting point of 163°–164° C.

Preparation of decahydro-3H,5H-benzo[ij]quinolizine-3,5-dione (7aα, 10aα, 10bα)

A solution of 10 g (0.044 mol) of the (4aα, 8β, 8aα) form of decahydro-2-oxo-8-quinolinepropanoic acid is prepared in 50 g of acetic anhydride. The mixture is stirred and refluxed 15 minutes. The acetic acid and unreacted acetic anhydride is removed at reduced pressure and the residue is treated with anhydrous diethyl ether. The residue crystallizes. The desired decahydro-3H,5H-benzo[ij]quinolizine-3,5-dione (7aα, 10aα, 10bα) has a melting point of 95°–97° C. after trituration with anhydrous diethyl ether.

EXAMPLE 6

Synthesis of Cycloheptanone 2,7-diacetic acid dimethyl ester

A solution of cycloheptanone pyrrolidine enamine (10.0 g, 0.06 mol), di-isopropylethylamine (23.3 g, 0.18 mol) in freshly distilled acetonitrile (150 ml) is treated dropwise with methyl bromoacetate (27.5 g, 0.18 mol). The mixture is stirred at reflux for 88 hours, concentrated and partitioned between water (150 ml) and chloroform (5×150 ml). The combined chloroform extracts are dried (MgSO$_4$), concentrated, and distilled to yield cycloheptanone 2,7-diacetic acid dimethyl ester, bp 123°–125° C. at 0.6 mm.

NMR (CDCl$_3$)δ1.31–2.05 (br. m., 8H), 2.12–3.45 (m, 6H), 3.32 (s, 6H).

Synthesis of Cycloheptane O-methyloxime 2,7-diacetic acid dimethylester

A solution of cycloheptanone 2,7-diacetic acid dimethyl ester (66.8 g, 0.26 mol) and methoxyamine hydrochloride (21.7 g, 0.26 mol) in pyridine (300 ml) is stirred at 25° C. for five days and at 55° C. for 24 hours. Additional methoxyamine hydrochloride (10.8 g, 0.13 mol) is added and the mixture is heated at 80° C. for 18 hours. The solution is poured into water (1 l) and extracted with chloroform (5×250 ml). The extracts are dried (MgSO$_4$) filtered and concentrated at reduced pressure.

The product is purified by flash chromatography on silica gel (elution with hexane:ethyl acetate 4:1).

NMR (CDCl$_4$)δ1.21–1.96 (br. m., 8H), 2.15–2.95 (m, 6H), 3.27 (s, 3H), 3.37 (s, 6H).

Synthesis of ±Cyclohepta[b]pyrrole-8-acetic acid, decahydro-2-oxo-, (3aα, 8β, 8aα)-; ±Cyclohepta[b]pyrrole-8-acetic acid, decahydro-2-oxo-, (3aα, 8α, 8aα)-; ±Cyclohepta[b]pyrrole-8-acetic acid, decahydro-2-oxo-, (3aα, 8β, 8aβ)-and methyl esters A solution of cycloheptanone O-methyloxime 2,7-diacetic acid methyl ester (58.1 g, 0.18 mol) in methanol (500 ml) is treated with 10% Rh/C (5 g) and hydrogen gas at 50 psi. After the hydrogen gas absorption is completed, the solution is filtered and concentrated to yield the product as an oily solid. The oily solid is triturated with anhydrous diethyl ether and filtered. The mixture of the three methyl ester products had mp 129°–134° C.

NMR (CDCl$_3$)δ1.24–1.85 (br. m., 8H), 2.00–2.62 (m, 5H), 2.63 (m, ½H), 2.83 (m, ½H), 3.22 (br. t., 0.05H, J=(Hz), 3.52 (dd, 0.8H, J=10 Hz, 8 Hz), 3.83 (dd, 0.45H, J=9 Hz, 2.3 Hz), 5.81 (br. s., 0.05H), 6.43 (br. s., 0.5H), 6.65 (br. s., 0.45H).

A mixture of ±cyclohepta[b]pyrrole-8-acetic acid, methyl ester, decahydro-2-oxo-, (3aα, 8β, 8aα)-; ±cyclohepta[b]pyrrole-8-acetic acid, methyl ester, decahydro-2-oxo-, (3aα, 8α, 8aα)-; ±cyclohepta[b]pyrrole-8-acetic acid, methyl ester, decahydro-2-oxo-, (3aα,8β,-8aβ)- (5 g, 0.022 mol) and 2N sodium hydroxide solution (11 ml) is stirred until hydrolysis is complete (TLC). The solution is treated with 2N hydrochloric acid (11 ml) and cooled in a refrigerator. The acid products as a white solid are removed by filtration and dried in vacuo, mp 178°–192° C.

NMR (DMSO, d$_6$)δ1.17–2.64 (br. m., 14H), 3.40 (m, 0.1H), 3.57 (dd, 0.6H, J=10 Hz, 5 Hz), 3.73 (br. d., 0.3H, J=10 Hz), 7.41 (br. s., 0.3H), 7.67 (br. s., 0.6H), 7.76 (br. s., 0.1H).

Synthesis of 2H-cyclohepta[gh]pyrrolizine-2,4(1H)-dione, octahydro-, (5aα, 9aα, 9bα)-; ±2H-cyclohepta-[gh]pyrrolizine-2,4(1H)-dione,octahydro-,(5aα, 9aβ, 9bα)-; 2H-cyclohepta[gh]pyrrolizine-2,4(1H)-dione, octahydro-,(5aα, 9aα, 9bβ)

A solution of ±cyclohepta[b]pyrrole-8-acetic acid, decahydro-2-oxo-, (3aα, 8β, 8aα)-, ±cyclohepta[b]pyrrole-8-acetic acid, decahydro-2-oxo-, (3aα, 8α, 8aα)- and cyclohepta[b]pyrrole-8-acetic acid, decahydro-2-oxo-, (3aα, 8β, 8aβ) - (8.16 g, 0.039 mol) in acetic anhydride (35 ml) is refluxed for 30 minutes and allowed to stand at room temperature 72 hours. The solution is concentrated at reduced pressure and triturated with anhydrous diethyl ether. Recrystallization (n-heptane) yields a mixture of 2H-cyclohepta[gh]pyrrolizine-2,4(1H)-dione, octahydro-, (5 aα, 9 aα, 9 bα)-; 2H-cyclohepta[gh)pyrrolizine-2,4(1H)-dione, octahydro-, (5aα, 9aβ, 9bα)-; ±2H-cyclohepta[gh]pyrrolizine-2,4(1H)-dione,octahydro-, (5aα, 9aα, 9bβ) with mp 80°–87° C.

NMR (CDCl$_3$)δ1.23–1.76 (br. m., 6H), 1.90–2.07 (m, 3H), 2.22–2.40 (m, 2H), 2.47–2.61 (m, 1H), 2.65–2.74 (m, 1H), 2.88 (dd, 1H, J=17.3 Hz, 7.9 Hz), 3.80 (br. t., 0.1 H, J=10 Hz), 4.01 (br. t., 0.6H, J=9.8 Hz), 4.52 (t., 0.3H, J=6.2 Hz).

EXAMPLE 7

Synthesis of cyclooctanone O-methyloxime 2,8-diacetic acid dimethyl ester

A solution of cyclooctanone pyrrolidine enamine (68.1 g, 0.38 mol); and di-isopropylethylamine (147.3 g, 1.14 mol) in freshly distilled acetonitrile (500 ml) is treated dropwise with methyl bromoacetate (174.3 a, 1.14 mol) and the mixture is stirred and refluxed for 18 hours. A solution of methoxyamine hydrochloride (33.4 g, 0.4 mol) in pyridine (200 ml) is added. The solution is stirred at room temperature for two hours. The solution is poured into water (500 ml) and extracted with diethylether (5×500 ml). The combined extracts are dried (MgSO$_4$), filtered, and concentrated to yield crude cyclooctanone o-methyloxime 2,8-diacetic acid dimethyl ester that is used as is.

Synthesis of ±1H-cycloocta[b]pyrrole-9-acetic acid methyl ester, decahydro-2-oxo-, (3aα, 9β, 9aα)-; ±1H-cycloocta[b]pyrrole-9-acetic acid methyl ester, decahydro-2-oxo-, (3aα, 9β, 9aβ)-; ±1H-cycloocta[b]pyrrole-9-acetic acid methyl ester, decahydro-2-oxo-, (3aα, 9α, 9aα)

A solution of cyclooctanone O-methyloxime 2,8-diacetic acid dimethyl ester (44.9 g, 0.15 mol) in methanol (500 ml) is treated with 10% Rh/C (20 g) and hydrogen gas at 50 psi. After hydrogen uptake is completed the solution is filtered to remove the catalyst and concentrated at reduced pressure. The resulting oil is chromatographed on silica gel (elution with chloroform:isopropanol; 97:3) to yield ±1H-cycloocta[b]pyrrole-9-acetic acid methyl ester, decahydro-2-oxo-, (3aα, 9β, 9aα), ±1H-cycloocta[b]pyrrole-9-acetic acid methyl ester, decahydro-2-oxo-,(3aα, 9α, 9aα)-, 1H-cyclooc-ta[b]pyrrole-9-acetic acid methylester, decahydro-2-oxo-, (3aα, 9β, 9aβ)- as a white solid that is used as is.

Synthesis of ±1H-cycloocta[b]pyrrole-9-acetic acid,
  decahydro-2-oxo-, (3aα, 9β, 9aα)-;
±1H-cycloocta[b]pyrrole-9-acetic acid,
  decahydro-2-oxo-, (3aα, 9α, 9aα)-;
±1H-cycloocta[b]pyrrole-9-acetic acid,
  decahydro-2-oxo-, (3aα, 9β, 9aβ)

A suspension of ±1H-cycloocta[b]pyrrole-9-acetic acid methyl ester, decahydro-2-oxo-, (3aα, 9β, 9aα)-; ±1H-cycloocta[b]pyrrole-9-acetic acid methyl ester, decahydro-2-oxo, (3aα, 9α, 9aα)-; 1H-cycloocta[b]pyrrole-9-acetic acid methyl ester, decahydro-2-oxo, (3 aα, 9β, 9aβ) - (3.0 g, 0.013 mol) in 2N NaOH (6.5 ml) is stirred until hydrolysis is complete. The basic solution is treated with 2N HCl (6.5 ml). The solution is cooled and the product is separated by filtration. After drying in vacuo ±1H-cycloocta[b]pyrrole-9-acetic acid, decahydro-2-oxo-, (3aα, 9β, 9aα)-; ±1H-cycloocta[b-]pyrrole9-acetic acid, decahydro-2-oxo-, (3aα, 9α, 9aα)-; ±1H-cycloocta[b]pyrrole-9-acetic acid, decahydro-2-oxo(3aα, 9β, 9aβ)- are isolated as a crystalline solid.

Synthesis of
cycloocta[gh]pyrrolizine-2,4(1H,5H)-dione,
  octahydro-, (5aα, 10aα, 10bα)-;
±cycloocta[gh]pyrrolizine-2,4(1H,
  5H)-dione,octahydro-, (5aβ, 10aβ, 10bα)-;
cycloocta[gh]pyrrolizine-2,4(1H,5H)dione, octahydro-,
  (5aα, 10aβ, 10bα)

A solution of ±1H-cycloocta[b]pyrrole-9-acetic acid, decahydro-2-oxo-, (3aα, 9β, 9aα)-; ±1H-cylooc-ta[b]pyrrole-9-acetic acid,decahydro-2-oxo, (3aα, 9α, 9aα)-; ±1H-cycloocta[b]pyrrole-9-acetic acid, decahydro-2-oxo-, (3aα, 9β, 9aβ) (2.8 g, 0.012 mol) in acetic anhydride is heated at reflux for 30 minutes and allowed to cool to room temperature overnight. The solution is concentrated at reduced pressure and the resulting solid is triturated with anhydrous diethyl ether. Sublimation (120° C., 0.1 mm) yields cycloocta[gh]pyrrolizine-2,4-(1H, 5H)-dione, octahydro-, (5aα, 10a α, 10bα)-; ±cy-cloocta[gh]pyrrolizine-2,4(1H,5H)-dione, octahydro-, (5aβ, 10aβ, 10bα)-; cycloocta[gh]pyrrolizine-2,4(1H,5H)dione,octahydro-, (5aα, 10aβ, 10bα)- with mp 121°–124° and 132°–134° C.

NMR (CDCl₃)δ1.08–1.99 (br. m., 10H), 2.13–2.72 (br. m., 5H), 2.99–3.16 (m, 1H), 3.78 (t, 0.2H, J=8.7 Hz), 4.07 (dd, 0.5H, J=9.9, 7.7 Hz), 4.54 (t, 0.3H, J=5.3 Hz).

We claim:
1. A compound having the structural formula I:

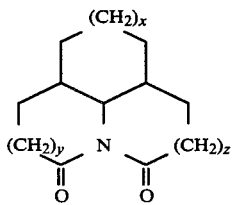

wherein x is zero; one, two, or three and y and z are independently zero or one.

2. A compound in accordance with claim 1 wherein x is zero.

3. A compound in accordance with claim 2 wherein x and y are zero.

4. A compound in accordance with claim 2 wherein x is one and y is zero.

5. A compound in accordance with claim 2 wherein x and y are one.

6. A compound in accordance with claim 1 wherein x is one.

7. A compound in accordance with claim 6 wherein y and z are zero.

8. A compound in accordance with claim 6 wherein y is one and z is zero.

9. A compound in accordance with claim 6 wherein y and z are one.

10. A compound in accordance with claim 1 where y and z are zero.

11. A compound in accordance with claim 10 where x is two.

12. A compound in accordance with claim 10 where x is three.

13. A compound in accordance with claim 3 having the name hexahydro-2H-cyclopenta[gh]pyrrolizine-2,4(1H)-dione (5aα, 7aα, 7bα).

14. A compound in accordance with claim 4 selected from the group consisting of octahydrocyclopent[hi]in-dolizine-2,4-dione (6aα, 8aα, 8bα) and octahydrocyclopent[hi]indolizine-2,4-dione (6aα, 8aβ, 8bβ).

15. A compound in accordance with claim 5 selected from the group consisting of hexahydro-1H-cyclopenta[ij]quinolizine-3,5(2H,6H)-dione (7aα, 9aα, 9bα);
  hexahydro-1H-cyclopenta[ij]quinolizine-3,5-(2H,6H)-dione (7aα, 7aα, 9bβ); and
  hexahydro-1H-cyclopenta[ij]quinolizine-3,5(2H,6H)-dione (7aα, 9aβ, 9bα).

16. A compound in accordance with claim 7 selected from the group consisting of hexahydropyrrolo[3,2,1-hi]indole-2,4(1H,5H)dione (5aα, 8aα, 8bα);
  hexahydropyrrolo[3,2,1-hi]indole-2,4(1H,5H)dione (5aα, 8aβ, 8bα); and
  hexahydropyrrolo[3,2,1-hi]indole2,4(1H,5H)-dione 5aα, 8aα, 8bβ).

17. A compound in accordance with claim 8 selected from the group consisting of octahydro-4H-pyr-rolo[3,2,1-ij]quinoline2,4(1H)-dione (6aα, 9aα, 9bα);
  octahydro-4H-pyrrolo[3,2,1-ij]quinoline-2,4(1H)-dione (6aα, 9aα, 9bβ);
  octahydro-4H-pyrrolo[3,2,1-ij]quinoline-2,4(1H)-dione (6aα, 9aβ, 9bα); and
  octahydro-4H-pyrrolo[3,2,1-ij]quinoline-2,4(1H)-dione (6aα, 9aβ, 9bβ).

18. A compound in accordance with claim 9 selected from the group consisting of decahydro-3H,5H-ben-zo[ij]quinolizine3,5-dione (7aα, 10aα, 10bα);
  a compound in accordance with claim 9 having the name decahydro-3H,5H-benzo[ij]quinolizine-3,5-dione (7aα, 10aβ, 10bα); and
  a compound in accordance with claim 9 having the name decahydro-3H,5H-benzo[ij]quinolizine-3,5-dione (7aα, 10aα, 10bβ).

19. A compound in accordance with claim 11 selected from the group consisting of octahydro-2H-cyclohepta[gh]pyrrolizine-2,4(1H)-dione, (5aα, 9aα, 9bα);
  octahydro-2H-cyclohepta[gh]pyrrolizine-2,4(1H)-dione (5aα, 9aβ, 9bα); and
  octahydro-2H-cyclohepta[gh]pyrrolizine-2,4(1H)-dione (5aα, 9aα, 9bβ).

20. A compound in accordance with claim 12 selected from the group consisting of octahydrocyclooacta[gh]pyrrolizine-2,4(1H, 5H)-dione (5aα, 10 aα, 10bα);
octrahydrocycloocta[gh]pyrrolizine-2,4(1H, 5H)-dione (5aα, 10aβ, 10bα); and
octahydrocycloocta[gh]pyrrolizine-2,4(1H, 5H)-dione (5aβ, 10aβ, 10bα).

21. A pharmaceutical composition comprising an amount of a compound in accordance with claim 1 effective to reverse electroconvulsive shock-induced amnesia, in combination with a pharmaceutically acceptable carrier.

22. A method of reversing electroconvulsive shock-induced amnesia in mammals comprising administering to said mammal a pharmaceutical composition in accordance with claim 21.

* * * * *